(12) United States Patent
Myrick et al.

(10) Patent No.: US 9,523,637 B2
(45) Date of Patent: Dec. 20, 2016

(54) THERMAL SELECTIVITY MULTIVARIATE OPTICAL COMPUTING

(75) Inventors: Michael L. Myrick, Irmo, SC (US); David L. Perkins, Irmo, SC (US); Ryan J. Priore, Columbia, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 619 days.

(21) Appl. No.: 13/553,381

(22) Filed: Jul. 19, 2012

(65) Prior Publication Data

US 2012/0279281 A1 Nov. 8, 2012

Related U.S. Application Data

(62) Division of application No. 11/576,359, filed as application No. PCT/US2005/035617 on Oct. 4, 2005, now Pat. No. 8,240,189.

(60) Provisional application No. 60/615,808, filed on Oct. 4, 2004.

(51) Int. Cl.
*G01N 29/02* (2006.01)
*G01N 21/3504* (2014.01)
*G01N 21/17* (2006.01)

(52) U.S. Cl.
CPC ... *G01N 21/3504* (2013.01); *G01N 2021/1704* (2013.01)

(58) Field of Classification Search
CPC .................................. G01N 21/17; G01N 29/02
USPC .......... 73/24.01, 24.02, 584, 64.35; 356/303, 356/417, 37; 250/341.8
See application file for complete search history.

(56) References Cited

U.S. PATENT DOCUMENTS

| | | | | |
|---|---|---|---|---|
| 4,499,378 A | * | 2/1985 | Miyatake | G01N 21/3504 250/343 |
| 5,616,826 A | * | 4/1997 | Pellaux | G01N 21/1702 250/343 |
| 6,006,585 A | * | 12/1999 | Forster | G01N 21/1702 250/343 |
| 7,245,374 B2 | * | 7/2007 | Hendriks | G01J 3/02 356/326 |
| 2004/0180448 A1 | * | 9/2004 | Lehmann | G01N 33/0013 436/151 |
| 2006/0176471 A1 | * | 8/2006 | Hendriks | G01J 3/02 356/39 |

OTHER PUBLICATIONS

Myrick et al., A single-element all-optical approach to chemomoetric prediction, Vibrational Spectroscopy, vol. 28, Issue 1, Feb. 28, 2002, pp. 73-81.*

* cited by examiner

*Primary Examiner* — Michael A Lyons
*Assistant Examiner* — Hoang Nguyen
(74) *Attorney, Agent, or Firm* — Haynes and Boone, LLP

(57) ABSTRACT

A method of using photoacoustic spectroscopy to determine chemical information about an analyte includes the steps of emitting a light ray for interaction with a sample of an analyte; transmitting the light ray through a fill fluid disposed in a detection cell, the fill fluid having molecules substantially similar to molecules of the analyte to absorb the light ray; producing a thermal wave and oscillation in the fill fluid proportional to an intensity of the light ray; including a pressure oscillation in the fill fluid by the thermal wave; and detecting the pressure oscillation by a microphone to determine information about the analyte sample.

11 Claims, 3 Drawing Sheets

THERMAL SELECTIVITY MULTIVARIATE OPTICAL COMPUTING

CROSS-REFERENCE TO RELATED APPLICATIONS

This application is a divisional of, and claims priority to, U.S. patent application Ser. No. 11/576,359, entitled "Thermal Selectivity Multivariate Optical Computing," filed Jul. 14, 2008 now U.S. Pat. No. 8,240,189, which was the National Stage of International Application No. PCT/US2005/035617, file Oct. 4, 2005, which claims the benefit of U.S. Provisional Application Ser. No. 60/615,808, entitled "Thermal Selectivity Multivariate Optical Computing," filed Oct. 4, 2004, each of which is hereby incorporated by reference in their entirety.

STATEMENT OF FEDERALLY SPONSORED RESEARCH OR DEVELOPMENT

This invention was made with Government support under grant number F33615-00-2-6059 awarded by the United States Air Force Research Laboratory. The Government has certain rights in this invention.

FIELD OF THE INVENTION

The present invention relates to filters that improve the precision of multivariate optical computing in spectroscopic analysis.

BACKGROUND OF THE INVENTION

The present invention relates to filters that improve the precision of multivariate optical computing Multivariate optical computing (MOC) is a predictive spectroscopy technique that incorporates a multi-wave-length spectral weighting directly into analytical instrumentation. The measurement precision of MOC has been studied for various techniques, several of which involve the use of an interference filter described as a multivariate optical element (MOE). Since MOE-based MOC uses detectors that see all wavelengths simultaneously—including wavelengths that carry no information—measurement noise is reduced and measurement precision is increased if the system can be made sensitive primarily to wavelengths carrying information.

In absorption/transmission/reflection measurements, the best measurement precision occurs when the detector responds only to those wavelengths where the sample analyte exhibits absorption. Thus, the ideal detector response would be one that only accumulates a signal where variance related to the analyte occurs in a data set. Such detection schemes are possible with thermal measurements as compared to purely optoelectronic detectors.

BRIEF SUMMARY OF INVENTION

The present invention is generally directed to thermal-based detectors that improve the precision of multivariate optical computing for spectroscopic analysis.

One type of thermal detection according to an aspect of the invention is based on photoacoustic spectroscopy. Photoacoustic detection offers a highly sensitive measurement scheme in the mid-infrared (MIR) far liquids, solids and gases by observing the thermal-wave decay of absorption-induced beating via a pressure oscillation in a sample cell. A photoacoustic detector using a fill gas (or liquid) composed of the analyte alone (or with a non-absorbing filler) will provide a detector that is sensitive primarily to the wavelengths absorbed by the analyte. The effective wavelength range utilized in a measurement using such a detector will only be of those wavelengths where the sample exhibits absorption-induced heating. Effectively, the analyte becomes the detector, and the multivariate optical element is designed to correlate the spectral variance in the photoacoustic signal with the analyte concentration. The photoacoustic cell can be filled with analyte to a concentration that provides optimal signal to noise, since the analyte filling the cell is not the sample being measured. Instead, the photoacoustic-analyte cell is used only as a detector for light passing through, emitted by, scattered from, or reflecting from the sample.

Among the additional types of detectors made for thermal selectivity are pyroelectric detectors, thermoelectric or thermopile detectors, bolometers. In each case, a reflective coating (for example, a gold metal film) on the original detector can be used to eliminate the broad wavelength sensitivity of the detector, while a polymer or liquid coating can be applied in a thin film atop the reflector to give sensitivity to analyte absorption bands.

In one aspect of the invention, a method of using photoacoustic spectroscopy to determine chemical information about an analyte includes the steps of emitting a light ray for interaction with a sample of an analyte; transmitting the light ray through a fill fluid disposed in a detection cell, the fill fluid having molecules substantially similar to molecules of the analyte to absorb the light ray; producing a thermal wave and oscillation in the fill fluid proportional to an intensity of the light ray; the thermal wave inducing a pressure oscillation in the fill fluid; and detecting the pressure oscillation by a microphone to determine information about the analyte sample. In this aspect, the analyte can be a gaseous analyte, a liquid analyte, a solid analyte, a dissolved analyte, a powdered analyte, an emulsified analyte, or combinations of these analytes. The analyte molecules can also be the same as the fill fluid molecules in this aspect.

Also in this aspect of the invention, the analyte can include a non-absorbing carrier fluid to absorb the light ray, which can be emitted from a broadband light source. The light ray interacts with the analyte in this aspect by being emitted through, emitted by, scattered from, or reflecting from the analyte.

Further in this aspect of the invention, the method can include the step of modulating an intensity of the light ray at a fixed frequency. A further step according to the method is to read a detector response at the fixed frequency. A wavelength of the light ray in this aspect can include a non-zero spectral weighting. Also in this aspect, the microphone records only the pressure oscillation induced by an absorbed wavelength of the light ray.

According to another aspect of the invention, a photoacoustic detection system includes a detection cell having a chamber and a port defined therein. The chamber is configured to hold a fill fluid and analyte, and a microphone detector is located in the port, the microphone detector being configured to record a pressure oscillation in the till fluid induced by the wavelengths of a light ray absorbed by the fill fluid such that information about the analyte can be determined. The pressure oscillation detected by the microphone detector provides information about the analyte.

The detection cell in this aspect of the invention includes an inlet for injecting the fill fluid and the analyte into the chamber. Further, the detection cell includes an outlet for releasing the fill fluid and the analyte franc the chamber.

Also in this aspect of the invention, the photoacoustic detection system can include a light source being configured to emit the light ray in a direction of the chamber. The light source can be a broadband light source. The light source can be configured to modulate an intensity of the light ray at a fixed frequency.

Further in this aspect of the invention, the photoacoustic detection system can include an oscilloscope in communication with the microphone detector, the oscilloscope being configured to present a system response based on the pressure oscillation. The system response is produced by a wavelength of the light ray with a non-zero spectral weighting.

Other aspects and advantages of the invention will be apparent from the following description and the attached drawings, or can be learned through practice of the invention.

BRIEF DESCRIPTION OF DRAWINGS

A full and enabling disclosure of the present invention, including the best mode thereof to one of ordinary skill in the art, is set forth more particularly in the remainder of the specification, including reference to the accompanying figures in which.

DETAILED DESCRIPTION OF THE INVENTION

Figure 1:
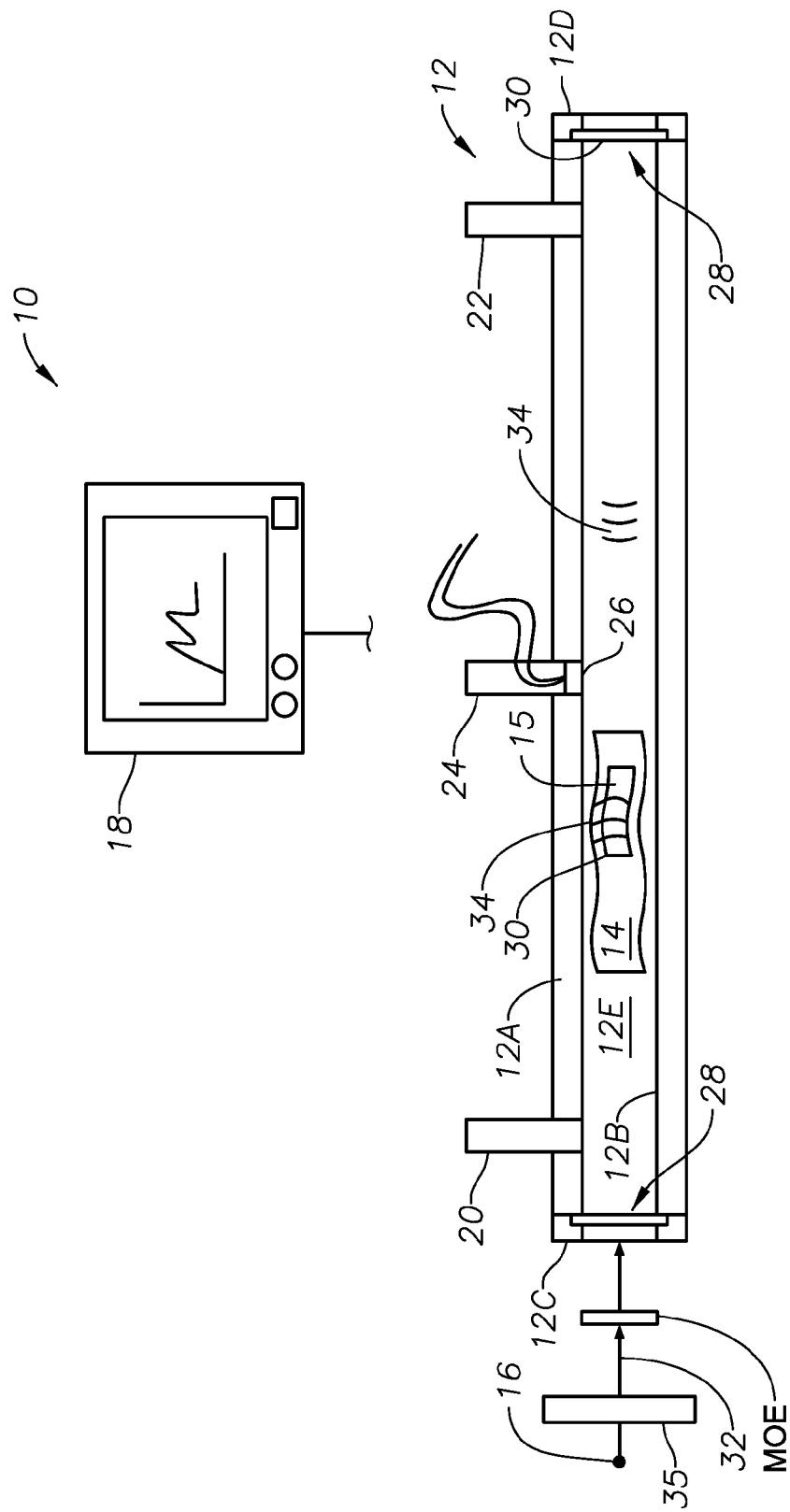
FIG. 1 is a schematic view of a photoacoustic infrared cell in a Fourier Transform instrument for measuring calibration spectra and collecting a photoacoustic signal according to an aspect of the invention.

Detailed reference will now be made to the drawings in which examples embodying the present invention are shown. Repeat use of reference characters in the drawings and detailed description is intended to represent like or analogous features or elements of the present invention.

The drawings and detailed description provides full and detailed written description of the invention and the manner mid process of making and using it, so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended claims and their equivalents.

Multivariate optical computing (MOC) according to some aspects of the present invention simplifies instrumentation and data analysis requirements of multivariate calibration.

As the figures generally show, a multivariate optical element (MOE) utilizes a thin film interference filter to sense magnitude of a spectral pattern. A no-moving-parts spectrometer, which is highly selective to a particular analyte, can be constructed by designing simple calculations based on the filter transmission and reflection spectra. A high throughput measurement can also be made since a broadband light source is used and many wavelengths are seen simultaneously at the detector.

Turning now to FIG. 1, a photoacoustic detection system is designated in general by the element number 10. The photoacoustic detection system 10 broadly includes a dual function, infrared gas cell or photoacoustic detection cell 12, a carrier fluid such as a gas 14, an analyte such as a vapor 15, a light source 16 and an oscilloscope 18. The dual function arises from use of a single cell to measure both light transmission spectra and photoacoustic spectra. More specifically, as described in detail below, the photoacoustic detection cell 12 may be used for measuring calibration spectra in a Fourier Transform instrument as well as for collecting a final photoacoustic signal regarding the vapor 15. Although the analyte 15 is a vapor in this example, this embodiment of the invention is not limited to a gaseous analyte. The analyte 15 can be a liquid analyte, a solid analyte, a dissolved analyte, a powdered analyte, or an emulsified analyte, or combinations of these.

Turning to one function of cell 12, i.e., as a photoacoustic detection cell, the photoacoustic detection cell 12 of FIG. 1 includes a plurality of surfaces and walls 12 A-D that form an interior or chamber 12 E. As shown, a carrier gas & vapor inlet port 20, a carrier gas and vapor outlet port 22 and a central port 24 are formed in the surface 12 A. The skilled artisan will appreciate that the number and shape of the surfaces and walls 12 A-D and the locations of the ports 20, 22 and 24 can be modified to suit various applications and are not limited to the example shown, and that detection can be performed with other tools than the oscilloscope 18.

FIG. 1 further shows that a microphone detector 26 is arranged in the central port 24, and one or more glass plates 28 are located in and help form the end walls 12C, 12D. As shown, the carrier gas 14 and the analyte vapor 15 are introduced into the chamber 12E via the carrier gas & vapor inlet port 20. The microphone detector 26 is connected to the oscilloscope 18 to record and analyze radiometric and photoacoustic measurements based on interaction a light rays or beams 32 with an interface or gaseous matrix 30 formed by the carrier gas 14 and the analyte vapor 15, as described in greater detail below.

FIGS. 2A-C generally show measurement precision examples comparing a system response to a T-R regression vector of a multivariate optical element, where T-R is a regression estimator ($t_r$).

Figure 2:
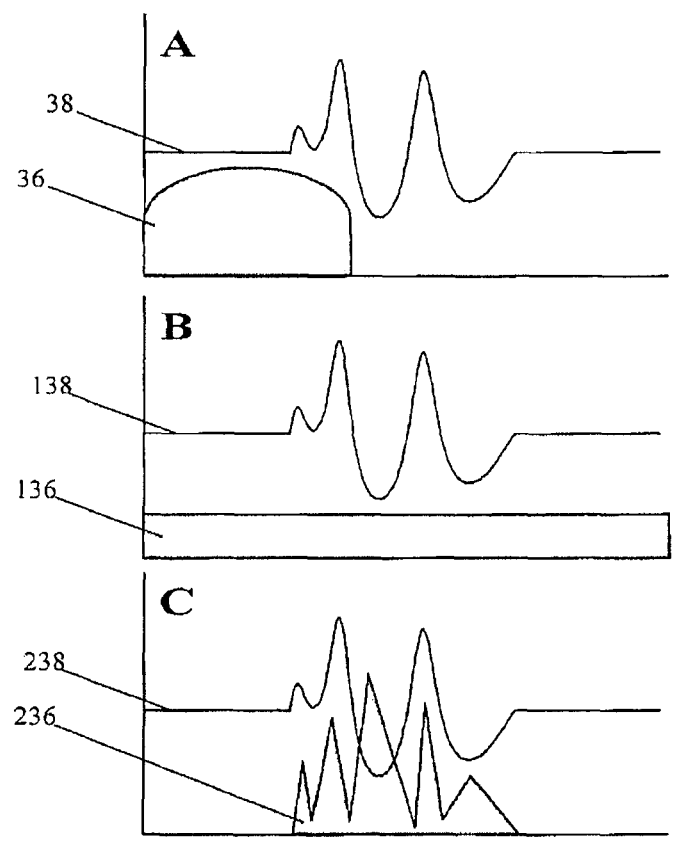
FIG. 2A is a graph comparing a system response to a regression vector of a multivariate optical element that would produce measurements with poor precision because the spectral sensitivity overlaps the spectral details poorly.
FIG. 2B is a graph similar to FIG. 2A showing a better detector response that would produce modest precision because, while sensitive to the important spectral window, the system also accumulates signal front wavelengths outside the important region.
FIG. 2C is a graph similar to FIG. 2A showing an ideal system response where only the wavelengths with a non-zero spectral weighting produce the system response according to another aspect of the invention.

Aspects of the invention may be better understood with reference to FIGS. 1-2C and to an exemplary method of operation.

Turning to the other function of cell 12, i.e., to measure transmission spectra of light rays, as shown in FIG. 1 and briefly introduced above, the dual function infrared gas cell 12 can be designed to be inserted directly into a spectrometer (for example, a FT-infrared spectrometer) so that the system response of this detector can be determined precisely.

As briefly introduced, photoacoustic spectroscopy is a specific thermal, non-destructive measurement of the interaction between the incident light rays 32 and the carrier gas 14 and the interface 30 via a non-radiative relaxation process. As shown in FIG. 1, the incident light rays 32 are emitted by the pulsed or chopped light source 16, which in this example is a broadband light source. The light passes through a sample 35, containing at least one gaseous analyte to be measured. After passing through the sample, the light rays 32 interact with the MOE, then enter the photoacoustic cell 12. The cell 12 is filled with a gaseous mixture of vapor of the same molecular type as the analyte 15, with possibly an inert/absorption-free carrier gas 14. The fill gas absorbs the incident light rays 32. This interaction produces a thermal wave 34 or heat proportional to the intensity of the incident beam 32, which oscillations can he detected by the microphone 26. By modulating the source 16 and thus the intensity of the incident radiation 32 at a fixed frequency, the detector response can be read at the reference frequency yielding a very precise measurement. Ultimately, the analyte-rich fill gas 15 becomes the detector since the microphone 26 only responds to those wavelengths that were absorbed by the fill gas 15.

The skilled artisan will understand that photos cons-tic detection is not limited to gases, but can be applied to liquids and even solids. Other types of thermal detectors can also be used to measure gases, liquids and solids by the method described here.

Turning now to FIG. 2A, poor precision is shown because there is little overlap between a system response 36 and a regression vector 38. In comparison, FIG. 2B shows moderate precision since the system response 136 is also accumulating a signal from wavelengths outside of a regression vector 138. In FIG. 2C, an ideal system response according to this aspect of the invention is shown in which only the wavelengths with a non-zero spectral weighting produce a system response 236, which correlates substantially with a regression vector 238.

Figure 3:
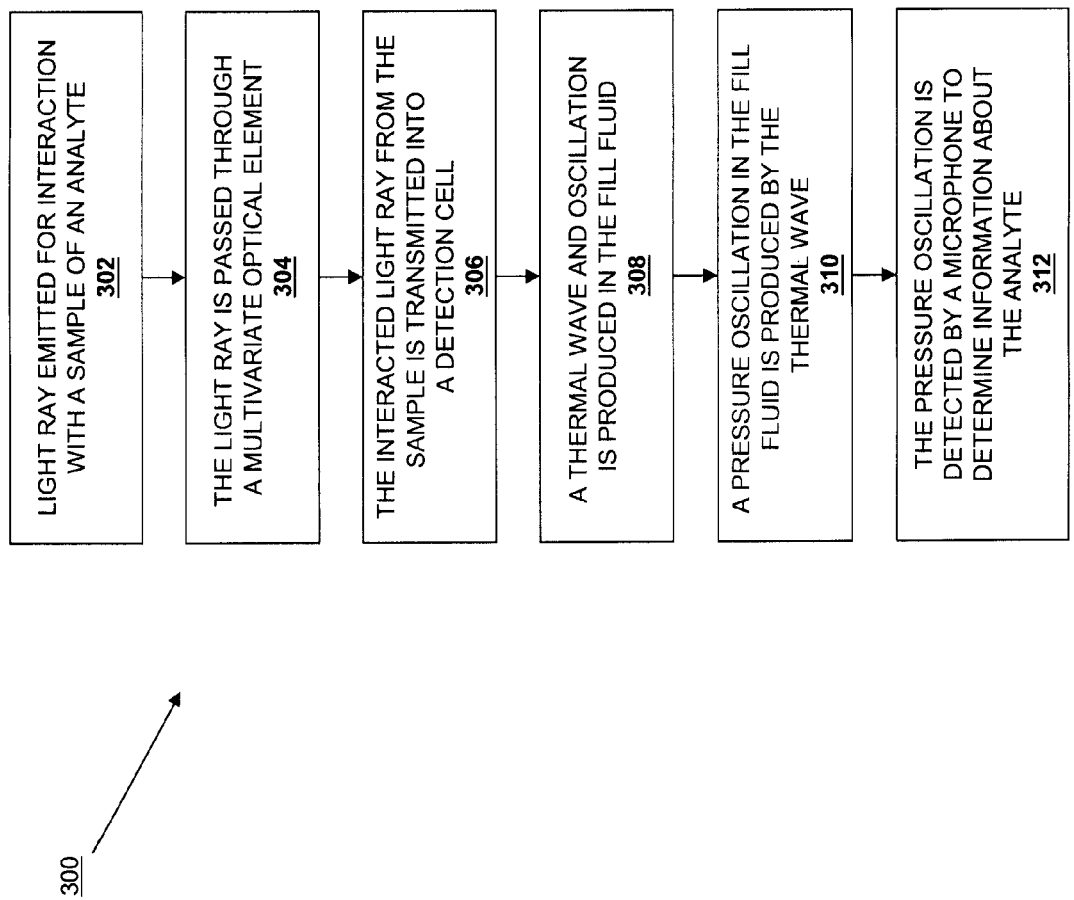
FIG. 3 illustrates the steps of the method of the invention.

Turning to FIG. 3, the steps of preferred methods of the invention are illustrated. In a method 300 for using photoacoustic spectroscopy to determine chemical information about a sample analyte, in step 302, a light ray is emitted for interaction with the sample analyte. In step 304, the light ray is passed through a multivariate optical element. In step 306, the interacted light ray from the sample is transmitted into a detection cell. The detection cell includes a fluid disposed therein and selected to have molecules of the sample analyte disposed to absorb the transmitted light ray. In step 308, a thermal wave and oscillation is produced in the fill fluid. The thermal wave is proportional to an intensity of the light ray. In step 310, a pressure oscillation in the fill fluid is produced by the thermal wave. Finally, in step 312, the pressure oscillation is detected by a microphone to determine information about the analyte.

While preferred embodiments of the invention have been shown and described, those skilled in the art will recognize that other changes and modifications may be made to the foregoing examples without departing from the scope and spirit of the invention. It is intended to claim all such changes and modifications as fall within the scope of the appended claims and their equivalents.

What is claimed is:

1. A photoacoustic detection system, comprising:
   a light source to emit a light ray that optically interacts with a sample comprising an analyte to be measured;
   a multivariate optical element through which the light ray passes;
   a detection cell having a chamber and a port defined therein, the chamber being configured to hold a fill fluid and an analyte, wherein the fill fluid analyte is the same as the sample analyte; and
   a microphone detector disposed in the port, the microphone detector being configured to record a pressure oscillation in the fill fluid induced by the wavelengths of the light ray absorbed by the fill fluid such that information about the sample analyte can be determined.

2. The photoacoustic detection system as in claim 1, wherein the detection cell includes an inlet defined therein, the inlet being configured to inject the fill fluid and the analyte into the chamber.

3. The photoacoustic detection system as in claim 1, wherein the detection cell includes an outlet defined therein, the outlet being configured to release the fill fluid and the analyte from the chamber.

4. The photoacoustic detection system as in claim 1, wherein the pressure oscillation detected by the microphone detector provides information about the sample analyte.

5. The photoacoustic detection system as in claim 1, wherein the light source is a broadband light source.

6. The photoacoustic detection system as in claim 1, wherein the light source is configured to modulate an intensity of the light ray at a fixed frequency.

7. The photoacoustic detection system as in claim 1, further comprising an oscilloscope in communication with the microphone detector, the oscilloscope being configured to present a system response based on the pressure oscillation.

8. The photoacoustic detection system as in claim 7, wherein the system response is produced by a wavelength of the light ray with a non-zero spectral weighting.

9. The photoacoustic detection system as in claim 1, wherein the fill fluid comprises at least one of a gaseous analyte, a liquid analyte, a solid analyte, a dissolved analyte, a powdered analyte, or an emulsified analyte.

10. The photoacoustic detection system as in claim 1, wherein the fill fluid comprises a substantially non-absorbing carrier fluid.

11. The photoacoustic detection system as in claim 1, wherein the detection cell is a single dual function detection cell that operates as an infrared gas cell or photoacoustic detection cell.

* * * * *

UNITED STATES PATENT AND TRADEMARK OFFICE
CERTIFICATE OF CORRECTION

| | | |
|---|---|---|
| PATENT NO. | : 9,523,637 B2 | Page 1 of 1 |
| APPLICATION NO. | : 13/553381 | |
| DATED | : December 20, 2016 | |
| INVENTOR(S) | : Michael L. Myrick et al. | |

It is certified that error appears in the above-identified patent and that said Letters Patent is hereby corrected as shown below:

On the Title Page

Related U.S. Application Data currently reads:
"Division of application No. 11/576,359, filed as application No. PCT/US2005/035617 on Oct. 4, 2005, now Pat. No. 8,240,189."

Related U.S. Application Data should read as:
-- Divisional of patent application Ser. No. 11/576,359 filed Jul. 14, 2008, now U.S. Pat. No. 8,240,189, which was the National Stage of International Application No. PCT/US2005/035617, filed Oct. 4, 2005. --

In the Specification

In Column 1, Line 12: please correct "file" to read as -- filed --.

Signed and Sealed this
Fourth Day of April, 2017

Michelle K. Lee
*Director of the United States Patent and Trademark Office*